(12) United States Patent
Kumar et al.

(10) Patent No.: US 7,456,309 B2
(45) Date of Patent: Nov. 25, 2008

(54) REUSABLE UNIVERSAL POLYMER SUPPORT FOR REPETITIVE OLIGONUCLEOTIDE SYNTHESIS

(75) Inventors: Pradeep Kumar, Delhi (IN); Kailash Chand Gupta, Delhi (IN)

(73) Assignee: Council of Scientific and Industrial Research (IN)

( * ) Notice: Subject to any disclaimer, the term of this patent is extended or adjusted under 35 U.S.C. 154(b) by 382 days.

(21) Appl. No.: 11/014,411

(22) Filed: Dec. 16, 2004

(65) Prior Publication Data

US 2006/0135759 A1    Jun. 22, 2006

(51) Int. Cl.
*C07C 69/67* (2006.01)
*C07C 69/013* (2006.01)

(52) U.S. Cl. .......................................... 560/129; 560/1
(58) Field of Classification Search ................... None
See application file for complete search history.

(56) References Cited

U.S. PATENT DOCUMENTS 6,030,782 A * 2/2000 Anderson et al. ............. 506/32
6,093,302 A * 7/2000 Montgomery ............... 205/122
6,169,194 B1 * 1/2001 Thompson et al. .......... 556/429

\* cited by examiner

*Primary Examiner*—Shaojia Anna Jiang
*Assistant Examiner*—Eric S Olson
(74) *Attorney, Agent, or Firm*—McDonnell Boehnen Hulbert & Berghoff LLP (57) ABSTRACT

The present invention provides a reusable, universal polymer support for repetitive oligonucleotide synthesis and a method of synthesis thereof.

16 Claims, 2 Drawing Sheets

DMTr = 4,4'-Dimethoxytrityl
DMAP = 4-Dimethylaminopyridine
TEA = Triethylamine
EDC = 1,2-Dichloroethane
TPP = Triphenylphosphine
BTCM = Bromotrichloromethane
$B^R$ = Protected nucleic base

Figure1

DMTr = 4,4'-Dimethoxytrityl
DMAP = 4-Dimethylaminopyridine
TEA = Triethylamine
EDC = 1,2-Dichloroethane
TCA = Trichloroacetic acid
HBTU = 2-(1H-benzotriazol-1-yl)-1,1,33-tetramethyluronium hexafluorophosphate
DTT = Dithiothreitol

Figure 2

REUSABLE UNIVERSAL POLYMER SUPPORT FOR REPETITIVE OLIGONUCLEOTIDE SYNTHESIS

FIELD OF INVENTION

The present invention relates to a reusable universal polymer support for repetitive Oligonucleotide synthesis and a method of synthesis thereof. More precisely, the invention relates to a process to employ the reusable universal polymer support for carrying out oligonucleotide synthesis repeatedly.

BACKGROUND AND PRIOR ART REFERENCES

Synthetic oligonucleotides and their modified analogous are finding numerous applications in diagnostics, therapeutics, molecular biology and agricultural sciences (Beaucage and Iyer, *Tetrahedron*, 1992, 48, 2223; Pon et al., *BioTechniques*, 1994, 17, 526; Agrawal, *Methods in Molecular Biology: Protocols for Oligonucleotides and Analogs*. Humana Press, Totowa, N.J., Vol. 20, 1993; Eckstein, *Oligonucleotides and Analogues: A Practical Approach*. IRL Press, Oxford, UK, 1992). Recently, the use of modified oligonucleotides as antigene as well as antisense agents (inhibitors of gene expression at transcription and translation stages) has opened up the doors to design and develop cost effective and rapid protocols for their synthesis and purification. In order to meet the current requirement of the oligonucleotides, the present day methodology is not viable and requires considerable attention to develop rapid and cost-effective methods. Recently, with the advent of labile protecting groups (phenoxyacetyl for adenine and guanine and isobutyryl or acetyl for cytosine; dimethylformamidine for adenine, guanine and cytosine; p-tert-butylphenoxyacetyl for adenine, cytosine and guanine), better coupling reagents, shorter coupling times, faster deprotection conditions, universal polymer supports and automated systems for their assembly have simplified the synthesis of a large number of oligonucleotides. However, for their use as therapeutics in future drug arena, the current need of the hour is to develop economical methods for assembly of such a large number of oligonucleotides in large quantities. Since solid phase oligonucleotide synthesis is, now-a-days, the most preferred method for their assembly, the polymer support itself accounts for almost one third of the total cost of the production of these molecules. Et would be of a great impact if the cost of the polymer support alone could be brought down. In our opinion, this could be done in three ways, viz., (i) to employ high loading polymer supports, where large quantities of oligonucleotides could be assembled on a relatively smaller amount of the support, (ii) to synthesize multiple oligonucleotides in tandem, and (iii) to employ reusable polymer support, so that it could be recycled for carrying out multiple oligonucleotide synthesis.

Conventional Method for Oligonucleotide Synthesis and Deprotection: (FIG. 1)

Figure 1:
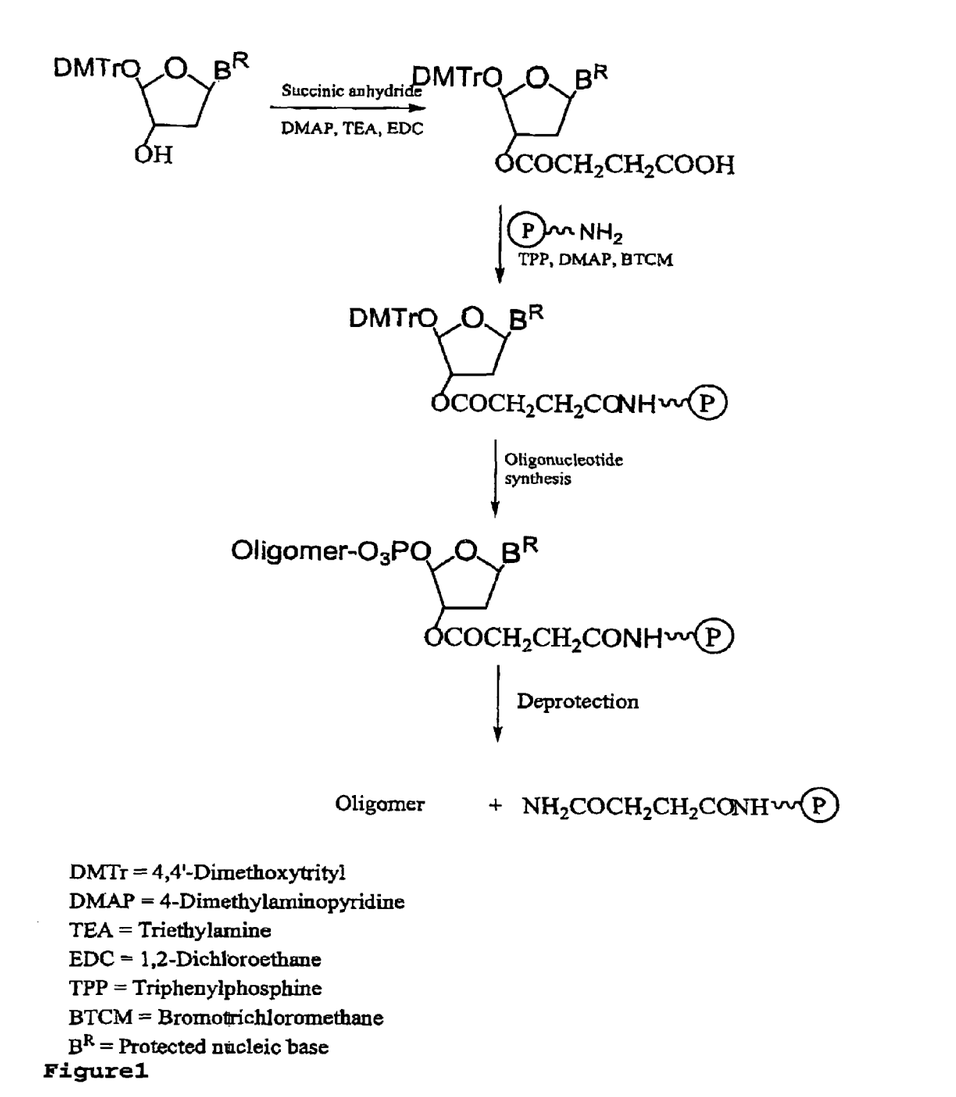
FIG. 1 illustrates a prior art method for oligonucleotide synthesis and deprotection using a non-reusable solid phase polymer support.

FIG. 1 describes conventional method for oligonucleotide synthesis and deprotection. Initial step comprises of reacting appropriately protected 2'-deoxyribonucleoside with a derivative of succinic acid (i.e. succinic anhydride) in the presence of a hypernucleophilic catalyst such as 4-dimethylaminopyridine (DMAP) to yield an appropriately protected 2'-deoxyribonucleoside-3'-O-succinate. In the subsequent reaction, this intermediate is reacted with aminoalkylated controlled pore glass in the presence of a suitable condensing reagent to obtain polymer supported leader nucleoside. In the FIG. 1, DMTr represents 4,4'-dimethyoxytrityl, B, a nucleobase and R is a protecting group (conventional/labile) as discussed above. The resulting polymer support after capping of residual amino groups is then used for conventional oligonucleotide synthesis, in an automated synthesizer, to produce an oligonucleotide of desired sequence attached to the linker arm. After synthesis of desired sequence, the chains are cleaved from the support under alkaline conditions. This step generates fully deprotected oligonucleotide and an amide-terminated polymer support, which can't be regenerated to another cycle of synthesis and hence goes waste.

The conventional methods are based mainly on aminoalkylated controlled pore glass (CPG), where the leader nucleoside is pre-attached via its 3'-hemisuccinate moiety, and the labile linkage is cleaved from the support with aqueous ammonium hydroxide treatment. This methodology suffers from a drawback that the polymer support, after a single use, is rendered unsuitable for refunctionalization for the next cycle of oligonucleotide synthesis. This problem has partly been addressed in recent reports, including those from the inventors' laboratory (Guzaev and Manoharan, *J. Am. Chem. Soc.* 2003, 125, 2380: Kumar et al., *Nucl. Acids Res.*, 2002, 30, e130; ibid, 1999, 27, e2; Azhayev, *Tetrahedron*. 1999, 55, 787: Ghosh et al., *J. Ind. Chem. Soc.*, 1998, 75, 206), wherein universal supports based on nucleosidic and non-nucleosidic linkages have been employed in the synthetic protocol. However, a polymer support that would permit repetitive syntheses (of the order of 25 or more) leading to multiple oligonucleotides is still elusive.

Considering the wide potential of such supports, some efforts have been made in this direction. In one such report, Hardy et al. (*Nucl. Acids Res.*, 1994, 22, 2998) have developed a method for producing more than one oligonucleotide per synthesis via a linker phosphoramidite called two oligomers per synthesis (TOPS). Using this reagent, two entirely different oligomers (synthesis of PCR primers) or multiple copies of a single oligomer could be generated in one continuous synthesis. After synthesis, aqueous ammonium hydroxide treatment releases either the pair of oligonucleotides or a single oligomer in large amount. The strategy further demands removal of terminal phosphate groups from the 3'-end, which requires harsh or prolonged deprotection conditions and non-quantitative dephosphorylation leaves unwanted impurities in the mixture.

In another report, Pon et al. (*J. Org. Chem.*, 2002, 67, 856) have developed a simple strategy called tandem oligonucleotide synthesis. The approach is simplified in a way that it allows the synthesis of two different isolable oligonucleotides. In this approach, the first oligonucleotide is synthesized on a succinylated support and 5'-hydroxyl of the first oligonucleotide is used as the starting point for the synthesis of second oligonucleotide after introducing a base labile hydroquinone-O,O'-diacetyl (Q) linker at 5'-hydroxyl group. The oligonucleotides can be cleaved from the support in sequential manner, if required. However, this approach along with the above one are limited to producing two different oligomers or one oligomer multiple times on a single polymer support. Moreover, selective cleavage, in the latter one, often leads to the contamination of one oligonucleotide into another one, which prevents the use of the synthesized primers in DNA sequencing and requires purification prior to their use. Furthermore, carboxylate derivatives of all the four nucleosides are required.

In more recent communications, Pon et al. (Pon et al., *Nucl. Acids Res.*, 1999, 27, 1541; *J. Chem. Soc., Perkin Trans 1* 2001, 2638) have reported (using LCAA-CPG support with generated hydroxyl groups on the surface and with the leader nucleoside molecule attached through a labile Q-linker) carrying out six cycles of oligonucleotide synthesis, albeit support functionalization with appropriately protected nucleosides has been claimed for 25 cycles. However, this system inherently admits of a limitation insofar as CPG is vulnerable to alkaline conditions and that repeated exposures to alkaline conditions (aq. ammonium hydroxide/methylamine) could affect the morphology of the glass support. They noticed this observation while using the reusable support for oligonucleotide synthesis in the seventh cycle and reported it in their later publication (*J. Chem. Soc., Perkin Trans* 1, 2000, 2638). Moreover, the above methodology also makes use of a non-conventional capping reagent (chloroacetic anhydride/methoxyacetic anhydride/p-tert-butylphenoxyacetic anhydride) for blocking residual hydroxyl groups on the polymer support. Moreover, at least four different pre-derivatized supports (dA, dC, dG and dT) would be required for all kinds of oligodeoxyribonucleotide synthesis. More recently, in yet another attempt, Pon and Yu have demonstrated the use of a new class of linker phosphoramidites (containing a cleavable 3'-ester linkage), for functionalization of supports in the machine itself. However, in this case also, the preparation of four nucleoside-linker phosphoramidites and the requirement of four additional ports in the machine for coupling of these linker molecules are the main limitations.

Therefore, there is a need to design a new polymer support, where (i) the preparation of all the four nucleoside (dA, dC, dG and T) derivatized polymer supports could be avoided, (ii) the oligomer sequences could be cleaved under non-ammoniacal conditions from the support, (iii) the cleaved support could easily be refunctionalized for repetitive oligonucleotide syntheses, (iv) the functionalization as well as oligomer cleavage procedures should be simple and straight-forward, and (v) fully deprotected oligomers could be obtained in single step. By taking these parameters in to consideration, the inventors have designed and synthesized a polymer support bearing a non-nucleosidic universal linker and a non-ammoniacal cleavable linker to avoid surface erosion during cleavage of oligomer sequences from the support.

OBJECTS OF INVENTION

The main objective of the present invention is to provide a novel polymer support for repititive oligonucleotide synthesis, which can take care of limitations of the prior art.

Another objective of the present invention is to design and synthesize a reusable universal polymer support for the repetitive synthesis of oligonucleotides.

Yet another objective of the present invention is to employ a universal linker to obviate the need to prepare a large number of pre-derivatized polymer supports for oligonucleotide syntheses.

Still another, objective of the invention is to incorporate a cleavable linker between polymer support and a universal linker to detach oligomer sequence from the polymer support under non-alkaline conditions.

Another objective is to refunctionalize the cleaved polymer support for another cycle of oligonucleotide synthesis.

Still another objective of the present invention is to provide a novel reusable universal polymer support for carrying out 25 or more cycle of oligonucleotides synthesis.

Yet another objective of the invention is to provide a method for the cleavage of oligonucleotides from the polymer support using non-alkaline conditions followed by removal of protecting groups (conventional and labile) from exocyclic amino functions of nucleic bases, internucleotidic phosphate functions and universal linker using commonly available reagents.

As mentioned in text, the term 'oligonucleotide' represents conventional unmodified oligonucleotides and modified analogs of oligonucleotides (backbone, base and terminal modified).

SUMMARY OF THE INVENTION

In the present invention, a mercaptoalkylated support is generated followed by its activation with a thiol specific reagent, 2,2'-dithiobis(5-nitropyridine). Subsequent steps involve reactions with DMTrO(CH$_2$)$_6$SH and 3% trichloroacetic acid to generate hydroxylated polymer support. Coupling of 2(3)-O-dimethoxytrityl-anhydroerythritol-3(2)-O-succinate with hydroxy-terminated support yields a universal polymer support, which may be used for oligonucleotide synthesis. An important feature of the synthesized polymer support is that the support obtained after cleavage of oligonucleotide chains may be refunctionalized and used for another cycle of synthesis of oligonucleotide sequence. Likewise, it may be used repeatedly for carrying out the synthesis process and this is for the first time that a polymer support could be used for 26 cycles of synthesis.

DETAILED DESCRIPTION OF THE INVENTION

Accordingly, the present invention provides a reusable universal polymer support for repititive Oligonucleotide synthesis and a method of synthesis thereof. The polymer support is of formula I:

Structure of polymer support (I)

where R1 is selected from a group consisting of substituted or unsubstituted alkyl group selected from —CH$_2$CH$_2$—, —CH(CH$_3$)$_n$CH$_2$—, —CH$_2$CH(CH$_3$)$_n$—, —CH(CH$_3$)$_n$CH(CH$_3$)$_n$—, —CH(CH$_2$OCH$_2$)CH—, —CH(CH$_2$CH$_2$CH$_2$)CH and n is the number of alkyl groups, selected from 1-6 and P is an organic or inorganic polymer support.

The invention also provides a method of synthesis of reusable polymer support of formula 1 and comprises:

The polymer support is selected from controlled pore glass (CPG) (500 A), (CPG) (1000 A), (CPG) (1400 A); (CPG) (3000 A), cross linked polystyrene, tentagel and merkogel.

The invention also provides a method for preparation of reusable polymer support of formula I, said process comprises steps of;

(i) treating the unmodified CPG with 3-mercaptopropyltriethoxysilane to obtain 3-mercaptopropylated CPG (ii) activating the support obtained in step (i) above with a thiol specific reagents DTNP to obtain an activated polymer support (iii) reacting the polymer support obtained in step (ii) with DMTrO(CH$_2$)$_6$SH followed by TCA in the range of 2-4% in dichloroethane to obtain a disulfide linkage containing hydroxyl-CPG (iv) coupling the universal linker, 2(3)-O-dimethoxytrityl-anhydroerythritol-3(2)-O-succinate, with the support obtained in step (iii) above in the presence of a condensing reagent to obtain a reusable universal polymer support (v) synthesizing an oligonucleotide sequence on the support obtained in step (iv) followed by cleavage of oligomer chains under non-alkaline conditions (vi) refunctionalizing the support obtained in step (v) after cleavage reaction repeating the steps (ii) to (iv) followed by synthesizing another cycle of oligomer sequence (vii) deprotecting the oligonucleotides completely obtained in step (v) with aq. Ammonium hydroxide containing spermine in the range of 0.5 to 2M and lithium chloride 0.25 to 0.7M for 8 h at a temperature in the range of 60-705° C.

In yet another embodiment the most preferred linkage cleavable under non-ammoniacal conditions, is disulfide.

In still another embodiment the thiol specific reagent for activation of mercaptoalkyl groups on the surface of polymer support is selected from 2,2'-dithiobispyridine (DTP), 2,2'-dithiobis(5'-nitropyridine) (DTNP), 4,4'-dithiobis(benzoic acid) (DTB).

In another embodiment the mercaptoalkanol used for the incorporation of disulfide linkage as well as hydroxyl groups is selected from O-(4,4'-dimethoxytrityl)-2-mercaptoethanol, O-(4,4'-dimethoxytrityl)-3-mercaptopropanol, O-(4,4'-dimethoxytrityl)-6-mercaptohexanol.

Yet another embodiment the detritylating reagent is selected from acetic acid, monochloroacetic acid (MCA), dichloroacetic acid (DCA), trichloroacetic acid (TCA).

In still another embodiment the condensing reagent is selected from dicyclohexylcarbodiimide, diisopropylcarodiimide, 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-succinimido-1,1,3,3-tetramethyluronium tetrafluoroborate (TSTU), 2-(3,4-dihydro-4-oxo-1,2,3-benzotriazin-3-yl)-1,1,3,3-tetramethyluronium tetrafluoroborate (TDBTU), 2-(2-oxo-1(2H)-pyridyl-1,1,3,3-tetramethyluronium tetrafluoroborate (TPTU), 2-(5-norbornene-2,3-dicarboximido)-1,1,3,3-tetramethyluronium tetrafluoroborate (TNTU), O-(7-azabenzotriazol-1-yl)-1,3-dimethyl-1,3-dimethyleneuronium hexafluorophosphate (HAMDU), O-(7-azabenzotriazol-1-yl)-1,3-dimethyl-1,3-trimethyleneuronium hexafluorophosphate (HAMTU), O-(7-azabenzotriazol-1-yl)-1,1,3,3-bis(pentamethylene)uronium hexafluorophosphate (HAPipU) for attaching the universal linker, 2(3)-(4,4'-methoxytrityl)anhydroerythritol-3(2)-hemisuccinate, to hydroxylated CPG support.

In another embodiment the reagent used for the non-ammonical cleavage of oligonucleotide chains from the support is selected from 2-mercaptoethanol (β-ME), dithiothreitol (DTT), dithioerythreitol (DTE).

In yet another embodiment the repeated synthesis of oligonucleotides is carried out on the polymer support of claim 1 following phosphoramidite chemistry employing conventional or labile protecting groups for nucleic bases In yet another embodiment the process for preparation of reusable universal polymer support of formula I, said process comprises steps of;
(i) treating the unmodified CPG with 3-mercaptopropyltriethoxysilane to obtain 3-mercaptopropylated CPG;
(ii) activating the support obtained in step (i) above with a thiol specific reagent, DTNP to obtain an activated polymer support;
(iii) reacting the polymer support obtained in step (ii) with DMTrO(CH$_2$)$_6$SH followed by TCA in the range of 2-4% in dichloroethane to obtain a disulfide linkage containing hydroxyl-CPG;
(iv) coupling universal linker namely 2(3)-O-dimethoxytrityl-anhydroerythritol-3(2)-O-succinate, with the support obtained in step (iii) above in the presence of a condensing reagent to obtain a reusable universal polymer support;
(v) synthesizing an oligonucleotide sequence on the support obtained in step (iv) followed by cleavage of oligomer chains under non-alkaline conditions, and
(vi) refunctionalizing the support obtained in step (v) after cleavage reaction repeating the steps (ii) to (iv) followed by synthesizing another cycle of oligomer sequence.
(vii) deprotecting the oligonucleotides completely obtained in step (v) with aq. ammonium hydroxide containing spermine in the range of 0.5 to 2M and lithium chloride 0.25 to 0.7M for a time period in the range of 6 to 10 hr. at a temperature in the range of 60-705° C.

In another embodiment in step III the preferred TCA concentration is 3% in dichloromethane.

In yet another embodiment in step (VII) the preferred spermine concentration is 1 M.

In another embodiment in step (VII) the preferred lithium chloride concentration is 0.5 M.

In yet another embodiment in step (VII) the preferred temperature is 65° C.

In still another embodiment in step (VII) the preferred time period is 8 hr.

In another embodiment in step (V) the oligonucleotide sequence represent conventional unmodified and modified analogs of oligonucleotides.

In another embodiment the modified oligonucleotide sequences represent modification at backbone, base and terminal of sequence.

Figure 2:
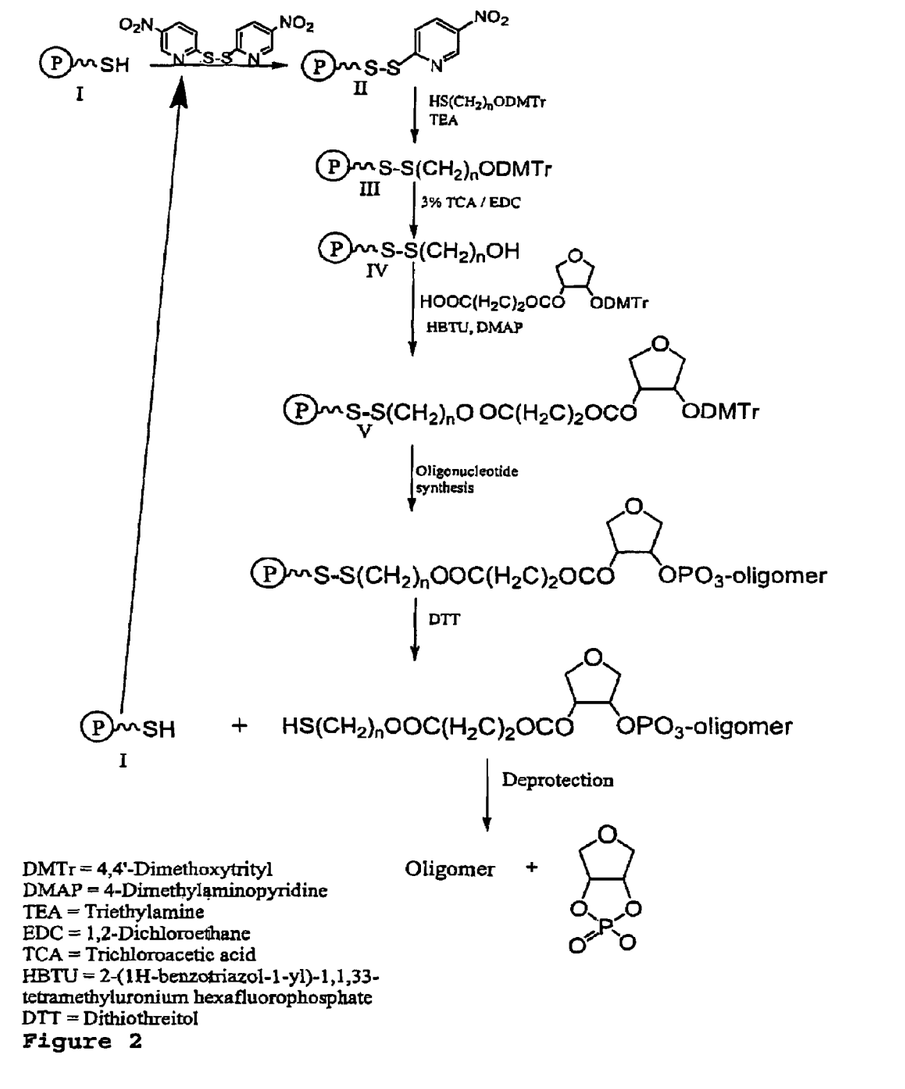
FIG. 2 illustrates the reusable solid phase synthesis methodology of the claimed invention in which the linker moiety is attached to the solid phase by a cleavable disulfide bond.

Oligonucleotide Synthesis According to Present Invention: (FIG. 2)

In the present invention a mercaptoalkylated support is generated followed by its activation with a thiol specific reagent, 2,2'-dithiobis(5-nitropyridine). Subsequent steps involve reactions with DMTrO(CH$_2$)$_6$SH and 3% trichloroacetic acid to generate hydroxylated polymer support. Coupling of 2(3)-O-dimethoxytrityl-anhydroerythritol-3(2)-O-succinate with hydroxyterminated support yields a universal polymer support, which may be used for oligonucleotide synthesis. An important feature of the synthesized polymer support is that the support obtained after cleavage of oligonucleotide chains may be refunctionalized and used for another cycle of synthesis of oligonucleotide sequence. Likewise, it may be used repeatedly for carrying out the synthesis process and this is for the first time that a polymer support could be used for 26 cycles of synthesis.

From above it is clear that the novelty of the present invention is the development of a new reusable universal polymer support for repetitive synthesis of oligonucleotides. Further, the synthesized oligomer sequences can be cleaved under non-ammoniacal condition and the polymer support can be regenerated for another cycle of oligonucleotide synthesis. Finally, these fully protected oligonucleotides can be deprotected under appropriate deprotection conditions (Table 1).

TABLE 1

Time needed for complete cleavage of oligomers under various conditions

|  | LiCl (0.5 M) | LiCl (1.0 M) | LiCl (1.5 M) |
|---|---|---|---|
| NH$_4$OH, 60° C. | 180 min | 60 min | 50 min |
| NH$_4$OH + MeNH$_2$ (1:1), 60° C. | 60 min | 40 min | 30 min |
| NH$_4$OH + Spermine (0.5 M), 60° C. | 120 min | 60 min | 30 min |
| NH$_4$OH + Spermine (1.0 M), 60° C. | 90 min | 60 min | 20 min |

The protecting groups employed for the protection of exocyclic amino functionalities of nucleic bases have the formula shown in the drawing accompany the specifications in which DMTr represents for 4,4'-dimethoxytrityl, n, number of alkyl groups and R1 is substituted or unsubstituted alkyl groups. The protecting group, viz., conventional (set I) and labile (set II-IV) used for exocyclic amino protection in nucleosides, as described below.

Set I: (Conventional Protecting Group)

B=Adenine; R=Benzoyl (Bz)

B=Cytosine; R=Acetyl (Ac)

B=Guanine; R=Phenoxyacetyl (Pac)

Set II: (Labile Protecting Group)

B=Adenine; R=Phenoxyacetyl (Pac)

B=Cytosine; R=Acetyl(Ac)

B=Guanine; R=Phenoxyacetyl (Pac)

Set III: (Labile Protecting Group)

B=Adenine; R=Dimethylformamidine (DMF)

B=Cytosine; R=Dimethylformamidine (DMF)

B=Guanine; R=Dimethylformamidine (DE)

Set IV: (Labile Protecting Group)

B=Adenine; R=p-tert-Butylphenoxyacetyl

B=Cytosine; R=:p-tert-Butylphenoxyacetyl

B=Guanine; R=:p-tert-Butylphenoxyacetyl

In an embodiment to the present invention, the support shown in the figure is a conventional polymer support. The nature of the support material is not restricted and may be selected from organic and inorganic supports. Thus, the polymer support for the synthesis of oligonucleotides may be selected from controlled pore glass (CPG) (500 A), CPG (1000 A), CPG (1400 A), CPG (3000 A), silica gel (porous or non-porous), cross-linked polystyrene, tentagel, merckogel and the like.

In yet another embodiment, the most preferred linkage, cleavable under non-ammonical conditions, is disulfide and the like.

In still another embodiment, the thiol specific reagent for activation of mercaptoalkyl groups on the surface of polymer support may be selected from 2,2'-dithiobispyridine, 2,2'-dithiobis(5-nitropyridine), 4,4'-dithiobis(benzoic acid) and the like.

In another embodiment, the mercaptoalkanol used for the incorporation of disulfide linker as well as free hydroxyl groups may be selected from O-(4,4'-dimethoxytrityl)-2-mercaptoethanol, O-(4,4'-dimethoxytrityl)-3-mercaptopropanol, O-(4,4'-dimethoxytrityl)-6-mercaptohexanol and the like.

In still another embodiment, the detritylating reagent may be selected from acetic acid, chloroacetic acid, dichloroacetic acid, trichloroacetic acid and the like.

In another embodiment, the coupling reagent may be selected from dicyclohexylcarbodiimide, diisopropylcarodiimide, 2-(1H-benzotriazol-1-yl)-1,1,3,3-tetramethyluronium hexafluorophosphate (HBTU), 2(1H-benzotriazol-1-yl)-1,1,3,3-tetramethyluronium tetrafluoroborate (TBTU), 2-succinimido-1,1,3,3-tetramethyluronium tetrafluoroborate (TSTU), 2-(3,4-dihydro-4-oxo-1,2,3-benzotriazin-3-yl)-1,1,3,3-tetramethyluronium tetrafluoroborate (TDBTU), 2-(2-oxo-1(2H)-pyridyl-1,1,3,3-tetramethyluronium tetrafluoroborate (TPTU), 2-(5-norbornene-2,3-dicarboximido)-1,1,3,3-tetramethyluronium tetrafluoroborate (TNTU), O-(7-azabenzotriazol-1-yl)-1,3-dimethyl-1,3-dimethyleneuronium hexafluorophosphate (HAMDU), O-(7-azabenzotriazol-1-yl)-1,3-dimethyl-1,3-trimethyleneuronium hexafluorophosphate (HAMTU), O-(7-azabenzotriazol-1-yl)-1,1,3,3-bis(pentamethylene)uronium hexafluorophosphate (HAPipU) and the like for attaching the universal linker, 2(3)-(4,4'-dimethoxytrityl)anhydroerythritol-3(2)-hemisuccinate, to hydroxylated support.

In still another embodiment, the substituted or unsubstituted alkyl groups (R1) nay be selected from —CH$_2$CH$_2$—, —CH(CH$_3$)CH$_2$—, —CH$_2$CH(CH$_3$)—, —CH(CH$_3$)CH (CH$_3$)—, —CH(CH$_2$OCH$_2$)CH—, —CH(CH$_2$CH$_2$CH$_2$) CH— and the like.

In yet another embodiment, the reagent used for the non-ammoniacal cleavage of oligonucleotide chains from the support may be selected from 2-mercaptoethanol (β-ME), dithiothreitol (DTT), dithioerythreitol (DTE) and the like.

Additional information about deprotection of oligonucleotides, attachment of universal linker, etc. may be found in the references (Gait, *Oligonucleotide Synthesis A Practical Approach*, IRL Press, Oxford, 1984; Agrawal, *Methods in Molecular Biology, Vol. 20: Protocols for Oligonucleotides and Analogs*, Humana Press, Totowa, N.J. 1993; Vaijayanthi et al., *Ind. J. Biochem. Biophys.*, 2003, 40, 377).

Preparation of Reusable Universal Polymer Support of FIG. 2

(i) 3-Mercaptopropylation of controlled pore glass (CPG) (MP-CPG): Unmodified CPG was treated with a 2% solution of 3-mercaptopropyltriethoxysilane in toluene.

(ii) Activation of mercaptopropyl-CPG: MP-CPG was activated with 2,2'-dithiobis(5-nitropyridine) in chloroform.

(iii) Hydroxy-CPG: Activated CPG obtained in the step (ii) was reacted with O-(4,4'-dimethoxytrityl)-6-mercaptohexanol in dichloroethane. Subsequently, the support was treated with 3% trichloroacetic acid in dichloroethane to generate hydroxy-CPG.

(iv) Coupling of universal linker: The hydroxy-CPG obtained in the step (iii) was reacted with 2(3)-(4,4'-dimethoxytrityl) anhydroerythritol-3(2)-hemisuccinate, the universal linker in the presence of a coupling reagent, HBTU, to obtain the reusable universal polymer support.

(v) Oligonucleotide synthesis: Oligonucleotides (homo- or heteropolymer) were assembled on the polymer support obtained in the step (iv) on a Pharmacia-LKB Gene Assembler Plus at 0.2 micromole scale.

(vi) Deprotection: After synthesis, the support bound oligomer was treated with methanolic DTT solution. The support recovered was washed thoroughly and refunctionalized following step (ii)-(iv) and used for another cycle of synthesis. The cleaved oligomer was concentrated and treated in a vial with aq. ammonium hydroxide (1 ml) containing spermine (1M) and lithium chloride (1.5M) at a temperature in the range of 60° to 80° C. for a duration of 10 min to 8 h (Table 1).

(vii) Desalting and analysis: The solution obtained in step (vi) was concentrated and desalted on a C-18 silica gel column. The eluted oligomer was concentrated and analyzed on RP-HPLC (column: C-18; buffer system: buffer A, 0.1M ammonium acetate, pH 7.1, solvent B: acetonitrile; flow rate: 1 ml/min; UV detector operating at 254 nm). Further characterization was carried out by MALDI-TOF mass spectra (matrix: 3-hydroxypicolinic acid; Seq IV from Kratos Inc. UK).

Embodiments of the invention will be illustrated in the following examples. Examples which should not construed as limiting the scope of the invention. In the examples, the following materials were used:

(i) CPG (500 A), DTNP, 2,2'-dithiobis(5-nitropyridine), and DMAP, 4-dimethylaminopyridine were commercially available from sigma Chemical Co., USA; HBTU, 2-(1H-benzotriazol-1-yl)-1,1,3,3-tetramethyluronium hexafluorophosphate, HATU, O-(7-azabenzotriazol-1-yl)-1,1,3,3-tetramethyluronium hexafluorophosphate and HOAT, 1-hydroxy-7-azabenzotriazole were obtained from Fluka AG, Switzerland;

(ii) Ammonium hydroxide solutions (~30%) and solvents were procured from local suppliers;

(iii) Cap A, a solution comprising acetic anhydride, sym-collidine and acetonitrile in a volume ratio of 1:1:8;

(iv) Cap B, a solution comprising 4-dimethylaminopyridine and acetonitrile in a ratio of 1:17;

(v) Oxidation solution, a solution comprising 0.05M $I_2$ in acetonitrile, $H_2O$ and sym. collidine in a volume ratio of 11:5:1;

In the following examples, the loading on the polymer supports was determined spectrophotometrically. In this procedure, polymer support (2-3 mg) was accurately weighed directly into a 10 ml volumetric flask. A solution of 3% trichloroacetic acid in 1,2-dichloroethane was then added to fill the flask. The contents were then thoroughly mixed for 5 min and the absorbance of the orange coloured solution was measured at 505 nm using a Perkin Elmer UV/VIS, Lambda-Bio 20 spectrophotometer. The loading was calculated in micromol/g of CPG as:

$$\text{Loading (micromol/g)} = \frac{A_{503} \times \text{Vol. (ml)} \times 1000}{\text{wt. of polymer support (mg)} \times 76}$$

wherein $A_{503}$=absorbance at 503 nm, Vol.=solution volume in ml, and Wt.=amount of CPG tested in mg.

The following examples are given by the way examples and therefore should not be constructed to limit the scope of the present invention.

EXAMPLE 1

Preparation of O-(4,41'-dimethoxytrityl)-2-mercaptoethanol

The above compound was prepared in two steps as follows:
2-Mercaptoethanol (10 mmol) was dried twice by co-evaporation with anhydrous pyridine (25 ml) and finally taken up in anhydrous pyridine (25 ml) followed by addition of 4,4'-dimethoxytrityl chloride (25 mmol) and 4-dimethylaminopyridine (5 mmol) at room temperature. The reaction mixture was stirred for 6 h and after monitoring the completion of reaction on tlc, methanol (1 ml) was added to the reaction. Solvent was removed under vacuum and the syrupy residue was redissolved in ethylacetate (150 ml) and washed sequentially with 5% aqueous solution of sodium bicarbonate (2×50 ml) and saturated solution of sodium chloride (2×50 ml). The organic phase was collected and concentrated under vacuum to obtain bis(4,4'-dimethoxytrityl)-mercaptoethanol as a syrupy residue.

The residue obtained was then taken up in chloroform (50 ml) containing 0.1% triethylamine and treated with a saturated solution of silver nitrate (50 mmol) dissolved in ethanol for 1 h at room temperature. After that, a solution of dithiothreitol (DTT) (70 mmol), dissolved in ethanol, was added and the reaction was allowed to stir for 30 min followed by removal of solid precipitate of silver complex from the reaction mixture. The filtrate was concentrated, the residue redissolved in ethylacetate (100 ml) and washed with water (3×50 ml). The organic phase was collected, concentrated under vacuum and purified by silica gel chromatography using an increasing gradient of methanol in 1,2-dichloroethane containing triethylamine (0.1%, v/v). The fractions containing the desired material were pooled together and concentrated to obtain O-(4,4'-dimethoxytrityl)-2-mercaptoalkanol in good yield (~78%).

EXAMPLE 2

Preparation of O-(4,4'-dimethoxytrityl)-3-mercaptopropanol

The above compound was prepared in two steps as follows:
3-Mercaptopropanol (10 mmol) was dried twice by co-evaporation with anhydrous pyridine (25 ml) and finally taken up in anhydrous pyridine (25 ml) followed by addition of 4,4' dimethoxytrityl chloride (25 mmol) and 4-dimethylaminopyridine (5 mmol) at room temperature. The reaction mixture was stirred for 6 h and after monitoring the completion of reaction on tlc, methanol (1 ml) was added to the reaction. Solvent was removed under vacuum and the syrupy residue was redissolved in ethylacetate (150 ml) and washed sequentially with 5% aqueous solution of sodium bicarbonate (2×50 ml) and saturated solution of sodium chloride (2×50 ml). The organic phase was collected and concentrated under vacuum to obtain bis(4,4'-dimethoxytrityl)-mercaptopropanol as a syrupy residue.

The residue obtained war, then taken up in chloroform (50 ml) containing 0.1% triethylamine and treated with a saturated solution of silver nitrate (50 mmol) dissolved in ethanol for 1 h at room temperature. After that, a solution of dithiothreitol (DTT) (70 mmol), dissolved in ethanol, was added and the reaction was allowed to stir for 30 min followed by removal of solid precipitate of silver complex from the reaction mixture. The filtrate was concentrated, the residue redissolved in ethylacetate (100 ml) and washed with water (3×50 ml). The organic phase was collected, concentrated under vacuum and purified by silica gel chromatography using an increasing gradient of methanol in 1,2-dichloroethane containing triethylamine (0.1%, v/v). The fractions containing the desired material were pooled together and concentrated to obtain O-(4,4'-dmethoxytrityl)-3-mercaptopropanol in ~80% yield.

EXAMPLE 3

Preparation of O-(4,4'-dimethoxytrityl)-6-mercaptohexanol

The above compound was prepared in two steps as follows:
6-Mercaptohexanol (10 mmol) was dried twice by co-evaporation with anhydrous pyridine (25 ml) and finally taken up in anhydrous pyridine (25 ml) followed by addition of 4,4'-dimethoxytrityl chloride (25 mmol) and 4-dimethylaminopyridine (5 mmol) at room temperature. The reaction mixture was stirred for 6 h and after monitoring the completion of reaction on tlc, methanol (1 ml) was added to the reaction. Solvent was removed under vacuum and the syrupy residue was redissolved in ethylacetate (150 ml) and washed sequentially with 5% aqueous solution of sodium bicarbonate (2×50 ml) and saturated solution of sodium chloride (2×50 ml). The organic phase was collected and concentrated under vacuum to obtain bis(4,4'-dimethoxytrityl)-6-mercaptohexanol as a syrupy residue.

The residue obtained was then taken up in chloroform (50 ml) containing 0.1% triethylamine and treated with a saturated solution of silver nitrate (50 mmol) dissolved in ethanol for 1 h at room temperature. After that, a solution of dithiothreitol (DTT) (70 mmol), dissolved in, ethanol, was added and the reaction was allowed to stir for 30 min followed by removal of solid precipitate of silver complex from the reaction mixture. The filtrate was concentrated, the residue redissolved in ethylacetate (100 ml) and washed with water (3×50 ml). The organic phase was collected, concentrated under vacuum and purified by silica gel chromatography using an increasing gradient of methanol in 1,2-dichloroethane containing triethylamine (0.1%, v/v). The fractions containing the desired material were pooled together and concentrated to obtain O-(4,4'-dmethoxytrityl)-6-mercaptohexanol in ~76% yield.

EXAMPLE 4

Preparation of Hydroxylated CPG

CPG (500 A, 1 g) was treated with a solution of 3-mercaptopropyltriethoxysilane (2%, v/v) in toluene for 2 h at 60° C. Then the support was recovered on a sintered disc glass funnel and washed extensively with toluene (3×25 ml) and diethylether (3×25 ml), respectively. In the subsequent reaction, mercaptopropylated polymer support was reacted with 2,2'-dithiobis(pyridine) (DTP) (5 mmol) in chloroform containing triethylamine (5 mmol) for 4 h with continuous shaking at room temperature. The support was again recovered on a sintered funnel and thoroughly washed with chloroform, methanol and diethylether (3×25 ml of each) to get rid of excess of reagent and 2-thiopyridone. Activated polymer support was subsequently treated with O-(4,4'-dimethoxytrityl)-2-mercaptoethanol (2.5 mmol) in dichloroethane containing triethylamine (0.5% v/v). The suspension was agitated for 2 h at room temperature and then the excess of reagents were removed by filtration on a sintered disc glass funnel followed by washing of the support with dichloroethane (3×25 ml) containing triethylamine (0.5%, v/v). The support was dried and loading on the polymer support was determined by perchloric acid method (Gait, *Oligonucleotide Synthesis: A Practical Approach*; IRL Press, Oxford, 1984).

In the next step, the polymer support was exposed to a solution of 3% trichloroacetic acid in dichloroethane (25 ml) for 5 min followed by filtration on a sintered disc glass funnel. The excess reagents were removed and the support thoroughly washed with dichloroethane (3×25 ml) and diethylether (3×25 ml), respectively to obtain free hydroxyl groups on the polymer support. Finally, it was dried under vacuum.

EXAMPLE 5

Preparation of Hydroxylated CPG

CPG (500 A, 1 g) was treated with a solution of 3-mercaptopropyltriethoxysilane (2%, v/v) in toluene for 2 h at 60° C. Then the support was recovered on a sintered disc glass funnel and washed extensively with toluene (3×25 ml) and diethylether (3×25 ml), respectively. In the subsequent reaction, mercaptopropylated polymer support was reacted with 2,2'-dithiobis(5-nitropyridine) (DTNP) (5 mmol) in chloroform containing triethylamine (5 mmol) for 4 h with continuous shaking at room temperature. The support was again recovered on a sintered funnel and thoroughly washed with chloroform, methanol and diethylether (3×25 ml of each) to get rid of excess of reagent and 5-nitropyridine-2-thione. Activated polymer support was subsequently treated with O-(4,4'-dimethoxytrityl)-2-mercaptoethanol (2.5 mmol) in dichloroethane containing triethylamine (0.5%, v/v). The suspension was agitated for 2 h at room temperature and then the excess of reagents were removed by filtration on a sintered disc glass funnel followed by washing of the support with dichloroethane (3×25 ml) containing triethylamine (0.5%, v/v). The support was dried and loading on the polymer support was determined by perchloric acid method (Gait, *Oligonucleotide Synthesis: A Practical Approach*; IRL Press, Oxford, 1984).

In the subsequent step, the tritylated polymer support was exposed to a solution of 3% trichloroacetic acid in dichloroethane (25 ml) for 5 min followed by filtration on a sintered disc glass funnel. The excess reagents were removed and the support thoroughly washed with dichloroethane (3×25 ml) and diethylether (3×25 ml), respectively to obtain hydroxylated CPG and then dried under vacuum.

EXAMPLE 6

Preparation of Hydroxylated CPG

CPG (500 A, 1 g) was treated with a solution of 3-mercaptopropyltriethoxysilane (2%, v/v) in toluene for 2 h at 60° C. Then the support was recovered on a sintered disc glass funnel and washed extensively with toluene (3×25 ml) and diethylether (3×25 ml), respectively. In the subsequent reaction, mercaptopropylated polymer support was reacted with 2,2'-dithiobis(pyridine) (DTP) (5 mmol) in chloroform containing triethylamine (5 mmol) for 4 h with continuous shaking at room temperature. The support was again recovered on a sintered funnel and thoroughly washed with chloroform, methanol and diethylether (3×25 ml of each) to get rid of excess of reagent and 2-thiopyridone. Activated polymer support was subsequently treated with O-(4,4'-dimethoxytrityl)-6-mercaptoethanol (2.5 mmol) in dichloroethane containing triethylamine (0.5%, v/v). The suspension was agitated for 2 h at room temperature and then the excess of reagents were removed by filtration on a sintered disc glass funnel followed by washing of the support with dichloroethane (3×25 ml) containing triethylamine (0.5%, v/v). The support was dried and loading on the polymer support was determined by perchloric acid method (Gait, *Oligonucleotide Synthesis: A Practical Approach*; IRL Press, Oxford, 1984).

Subsequently, the polymer support was exposed to a solution of 3% dichloroacetic acid in dichloroethane (25 ml) for 5 min followed by filtration on a sintered disc glass funnel. The excess reagents were removed and the support thoroughly washed with dichloroethane (3×25 ml) and diethylether (3×25 ml), respectively to obtain CPG support with free hydroxyl groups and finally, dried under vacuum.

EXAMPLE 7

Preparation of Hydroxylated CPG

CPG (500 A, 1 g) was treated with a solution of 3-mercaptopropyltriethoxysilane (2%, v/v) in toluene for 2 h at 60° C. Then the support was recovered on a sintered disc glass funnel and washed extensively with toluene (3×25 ml) and diethylether (3×25 ml), respectively. In the subsequent reaction, mercaptopropylated polymer support was reacted with 2,2'-dithiobis(pyridine) (DTP) (5 mmol) in chloroform containing triethylamine (5 mmol) for 4 h with continuous shaking at room temperature. The support was again recovered on a sintered funnel and thoroughly washed with chloroform, methanol and diethylether (3×25 ml of each) to get rid of excess of reagent and 2-thiopyridone. Activated polymer support was subsequently treated with O-(4,4'-dimethoxytrityl)-2-mercaptoethanol (2.5 mmol) in dichloroethane containing triethylamine (0.5%, v/v). The suspension was agitated for 2 h at room temperature and then the excess of reagents were removed by filtration on a sintered disc glass funnel followed by washing of the support with dichloroethane (3×25 ml) containing triethylamine (0.5%, v/v). The support was dried and loading on the polymer support was determined by perchloric acid method (Gait, *Oligonucleotide Synthesis: A Practical Approach*; IRL Press, Oxford. 1984).

In the next step, the disulfide linkage containing polymer support was exposed to a solution of 80% acetic acid in tetrahydrofuran (25 ml) for 5 min followed by filtration on a sintered disc glass funnel. The excess reagents were removed and the support thoroughly washed with tetrahydrofuran (3×25 ml) and diethylether (3×25 ml), respectively to obtain the hydroxyl groups bearing polymer support. Finally, it was dried under vacuum.

EXAMPLE 8

Preparation of Universal Linker Succinate

Butan-2,3-diol (2.0 mmol) was dimethoxytritylated using 4,4'-dimethoxytrityl chloride (1 mmol) in anhydrous pyridine (5 ml). The reaction was allowed to stir for 6 h at room temperature followed by quenching by addition of methanol (0.5 ml). After removal of solvent under reduced pressure, the residue was taken up in ethylacetate (50 ml) and washed sequentially with aqueous 5% sodium bicarbonate solution (2×15 ml) and saturated sodium chloride solution (2×10 ml). The organic phase was collected and dried over anhydrous sodium sulfate. After filtration, the solvent was removed on a rotavapor and subsequently purified on a silica gel column. The product, 2(3)-O-dimethoxytrityl-butan-3(2)-diol, was obtained in 85% yield. In the next step, 2(3)-O-dimethoxytrityl-butan-3(2)-diol (0.25 mmol) was dissolved in dichloroethane (5 ml) and added succinic anhydride (0.5 mmol), 4-dimethylaminopyridine (0.25 mmol) and triethylamine (0.25 mmol). The reaction was allowed to stir at room temperature for 1 h followed by dilution with dichloroethane (50 ml). The organic phase was washed with aqueous 5% citric acid solution (2×20 ml) and saturated sodium chloride solution (2×10 ml) followed by drying over anhydrous sodium sulfate. After filtration, the solvent was removed to obtain the hemisuccinate of 2(3)-O-dimethoxytrityl-butan-3(2)-diol in almost quantitative yield.

EXAMPLE 9

Coupling of Universal Tinker to Hydroxy-CPG

Hydroxyl-CPGs (1 g) prepared in examples 4-7 were coupled to a universal linker, 2(3)-(4,4'-dimethoxytrityl)anhydroerythritol-3(2)-hemisuccinate, (Kumar and Gupta, *Nucl. Acids Res.*, 1999, 27, e2) (1.0 mmol) using a condensing reagent, diisopropylcarbodiimide (1.0 mmol), in the presence of 4-dimethylaminopyridine (1 mmol) in 1,2 dichloroethane (15 ml). The reaction was allowed to stir overnight at room temperature followed by filtration on a sintered disc glass funnel. The recovered support was extensively washed with dichloroethane and diethylether (3×25 ml of each) containing triethylamine (0.1%, v/v). The residual hydroxyl groups on the support were capped by a solution consisting of acetic anhydride:triethylamine:1-methylimidazole:dichloroethane::1:1:0.4:6 for 1 h at room temperature followed by washings as discussed above. The loading on the support was determined spectrophotometrically as described above.

EXAMPLE 10

Coupling of Universal Linker to Hydroxy-CPG

Hydroxyl-CPGs (1 g) prepared in examples 4-7 were coupled to a universal linker, 2(3)-(4,4'-dimethoxytrityl)anhydroerythritol-3(2)-hemisuccinate, (Kumar and Gupta, Nucl. Acids Res., 1999, 27, e2) (1.0 mmol) using a condensing reagent, HBTU (1.0 mmol), in the presence of diisopropylethylamine (1.0 mmol) in acetonitrile (15 ml). The reaction was allowed to stir overnight at room temperature followed by filtration on a sintered disc glass funnel. The recovered support was extensively washed with acetonitrile and diethylether (3×25 ml of each) containing triethylamine (0.1%, v/v). The residual hydroxyl groups on the support were capped by a solution consisting of acetic anhydride:triethylamine:1-methylimidazole dichloroethane:: 1:1:0.4:6 for 1 h at room temperature followed by washings as discussed above. The loading on the supports was determined spectrophotometrically as described above.

EXAMPLE 11

Oligonucleotide Synthesis

One of the polymer supports obtained in examples 8 and 9 was used for carrying out oligonucleotide synthesis. The synthesis was carried out on Pharmacia LKB Gene Assembler Plus at 0.2 micromol scale following phosphoramidite chemistry. Coupling efficiency based on released dimethoxytrityl cation was found to be >98%.

A decamer oligomer, d(TTT TTT TTT T) (SEQ ID NO:1), was synthesized on the support. After synthesis, the oligomer bound polymer support was treated with a solution of 0.1M dithiothreitol in methanol (1 ml) containing triethylamine (0.1%, v/v) for 1 h at room temperature. After that, the supernatant was recovered by low speed (~3000 rpm) centrifugation and the support in the cassette was again washed with methanol (2×1 ml). The fractions were combined together and concentrated in vacuo. The polymer support, in the cas-

EXAMPLE 12

Support Reusability

In this Example, the support, used for oligonucleotide synthesis in example 10, after cleavage and refunctionalization, was again employed for carrying out second cycle of oligonucleotide synthesis. A second oligomer, d(TTT TTT TTT T) (SEQ ID NO:1), was synthesized and rest of the steps were followed as discussed in example 10.

EXAMPLE 13

Support Reusability

As discussed in examples 9 and 10, all the steps were followed to demonstrate the ability to recycle the polymer support for oligonucleotide synthesis. Following these steps, twenty five cycles of decamer synthesis, d(TTT TTT TTT T) (SEQ ID NO:1), were achieved without compromising the quality of the fully deprotected oligonucleotides.

EXAMPLE 14

Support Reusability

After cleavage of disulfide linkage in the twenty fifth cycle, refunctionalized polymer support was used for synthesis (26$^{th}$ cycle) of a primer sequence, d(TTC GTA CGT AGC GTC ATT TTC CCC) (SEQ ID NO:2), and subsequently used for a PCR amplification experiment after usual cleavage and deprotection steps.

EXAMPLE 15

Fully Deprotected Oligonucleotides, Analysis and Characterization

Fully protected oligonucleotide sequences cleaved from reusable support, obtained in the above examples, were subjected to the following treatment. The solid residue, in each case, was treated with aqueous ammonium hydroxide (30%, 1 ml) containing spermine (1M) and lithium chloride (0.5M) at 60° C. for 8 h to get rid of protecting groups from nucleic bases and internucleotidic phosphates. Then the solution was concentrated in vacuo, reconstituted in double distilled water (200 microliter) and desalted on a reverse-phase silica gel column. Elution of oligonucleotide chains was effected by 30% acetonitrile in water. The solution was concentrated and analyzed on RP-HPLC using a gradient of acetonitrile in ammonium acetate buffer, pH 7.1. These oligomers were then characterized by MALDI-TOF.

ADVANTAGES OF THE INVENTION

1. The process is simple and does not require expensive reagents and chemicals.

2. The process is clean and does not result in any side product formation

3. The employment of universal linker avoids the need to prepare a large number of pro derivatized polymer supports.

4. A non-ammoniacal cleavable linker prevents the erosion of glass based supports during cleavage of oligonucleotide chains from the support in aq. Ammonium hydroxide.

5. The fully deprotected oligonucleotides compare well with the standard oligonucleotides in respect to their retention time on HPLC and mass on MALDI-TOF.

6. Since entire process does not require any harsh/unusual cleavage/deprotection conditions, modified analogs of oligonucleotides can be assembled in a similar fashion.

---

What is claimed is:

1. A reusable universal polymer support for repetitive oligonucleotide synthesis having structural formula I:

Universal reusable polymer support, formula (I)

where, n is an integer independently selected from 1-6 and R1 is substituted or unsubstituted alkyl groups selected from —CH$_2$CH$_2$—, —CH (CH)$_n$CH$_2$—, —CH$_2$CH(CH$_3$)$_n$—, —CH(CH$_3$)$_n$CH(CH$_3$)$_n$—, —CH(CH$_2$OCH$_2$)CH—, —CH (CH$_2$CH$_2$CH$_2$)CH and P is an organic or inorganic polymer support.

2. The reusable universal polymer support claimed in claim 1, wherein the polymer support (P) is an inorganic or organic substance.

3. The reusable universal polymer support claimed in claim 2, wherein the polymer support (P) is selected from controlled pore glass (CPG) (500 A), (CPG) (1000 A), (CPG) (1400 A), (CPG) (3000 A), cross linked polystyrene, tentagel and merkogel.

4. A process for preparation of reusable universal polymer support of formula I, said process comprises steps of; (i) treating the unmodified CPG with 3-mercaptopropyltriethoxysilane to obtain 3-mercaptopropylated CPG; (ii) activating the support obtained in step (i) above with a thiol specific reagent, 2,2'-dithiobis(5'-nitropyridine) (DTNP) to obtain an activated polymer support; (iii) reacting the polymer support obtained in step (ii) with DMTrO(CH$_2$)$_6$SH followed by a detritylating regent in the range of 2-4% in dichloroethane to obtain a disulfide linkage containing hydroxyl-CPG, and (iv) coupling universal linker namely 2(3)-O-dimethoxytrityl-anhydroerythritol-3(2)-O-succinate, with the support obtained in step (iii) above in the presence of a condensing reagent to obtain a reusable universal polymer support.

5. The process as claimed in claim 4, wherein in step III the TCA concentration is 3% in dichloromethane.

6. The process as claimed in claim 4, wherein in step (i) CPG used is CPG (500 A).

7. The process as claimed in claim 4, wherein in step (ii) the thiol specific reagent of polymer support is selected from 2,2'-dithiobispyridine (DTP), 2,2'-dithiobis(5'-nitropyridine) (DTNP) and 4,4'-dithiobis(benzoic acid) (DTB).

8. The process as claimed in claim 4, wherein the detritylating reagent is selected from acetic acid, monochloroacetic acid (MCA), dichloroacetic acid (DCA), trichloroacetic acid (TCA).

9. The process as claimed in claim 4, wherein the condensing reagent is selected from dicyclohexylcarbodiimide, diisopropylcarodiimide, 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-succinimido-1,1,3,3-tetramethyluronium tetrafluoroborate (TSTU), 2-(3,4-dihydro-4-oxo-1,2,3-benzotriazin-3-yl)-1,1,3,3-tetramethyluronium tetrafluoroborate (TDBTU), 2-(2-oxo-1(2H)-pyridyl-1,1,3,3-tetramethyluronium tetrafluoroborate (TPTU), 2-(5-norbornene-2,3-dicarboximido)-1,1,3,3-tetramethyluronium tetrafluoroborate (TNTU), O-(7-azabenzotriazol-1-yl)-1,3-dimethyl-1,3-dimethyleneuronium hexafluorophosphate (HAMDU), O-(7-azabenzotriazol-1-yl)-1,3-dimethyl-1,3-trimethyleneuronium hexafluorophosphate (HAMTU), O-(7-azabenzotriazol-1-yl)-1,1,3,3-bis(pentamethylene) uronium hexafluorophosphate (HAPipU) for attaching the universal linker, 2(3)-(4,4'-dimethoxytrityl)anhydroerythritol-3(2)-hemisuccinate, to hydroxylated CPG support.

10. The process as claimed in claim 4, wherein the condensing reagent is selected from 2-mercaptoethanol (β-ME), dithiothreitol (DTT) and dithioerythreitol (DTE).

11. A method of using universal polymer support of formula I for repetitive oligunucleotide synthesis, said method comprises steps of; (i) treating the unmodified CPG with 3-mercaptopropyltriethoxysilane to obtain 3-mercaptopropylated CPG; (ii) activating the support obtained in step (i) above with a thiol specific reagent, 2,2'-dithiobis(5'-nitropyridine) (DTNP) to obtain an activated polymer support; (iii) reacting the polymer support obtained in step (ii) with DMTrO(CH$_2$)$_6$SH followed by trichloroacetic acid (TCA) in the range of 2-4% in dichloroethane to obtain a disulfide linkage containing hydroxyl-CPG, (iv) coupling universal linker namely 2(3)-O-dimethoxytrityl-anhydroerythritol-3(2)-O-succinate, with the support obtained in step (iii) above in the presence of a condensing reagent to obtain a reusable universal polymer support; (v) synthesizing an oligonucleotide sequence on the reusable universal polymer support obtained in step (iv) followed by cleavage of oligomer chains under non-alkaline conditions; (vi) refunctionalizing the reusable universal polymer support obtained in step (v) after cleavage reaction repeating the steps (ii) to (iv) followed by synthesizing another cycle of oligomer sequence, and (vii) deprotecting the oligonucleotides completely obtained in step (v) with aq. ammonium hydroxide containing spermine in the range of 0.5 to 2M and lithium chloride 0.25 to 0.7M for a time period in the range of 6 to 10 hr. at a temperature in the range of 60-75° C.

12. The method as claimed in claim 11, wherein in step III the TCA concentration is 3% in dichloromethane.

13. The method as claimed in claim 11, wherein in step (VII) the spermine concentration is 1 M.

14. The method as claimed in claim 11, wherein in step (VII) the lithium chloride concentration is 0.5 M.

15. The method as claimed in claim 11, wherein in step (VII) the temperature is 65° C.

16. The method as claimed in claim 11, wherein in step (VII) the time period is 8 hr.

* * * * *

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial
<220> FEATURE:
<223> OTHER INFORMATION: synthetic oligonucleotide

<400> SEQUENCE: 1
tttttttttt                                                          10

<210> SEQ ID NO 2
<211> LENGTH: 24
<212> TYPE: DNA
<213> ORGANISM: Artificial
<220> FEATURE:
<223> OTHER INFORMATION: synthetic oligonucleotide

<400> SEQUENCE: 2 tcgtacgta gcgtcatttt cccc                                           24
```